(12) United States Patent
Karkanias et al.

(10) Patent No.: US 7,914,419 B2
(45) Date of Patent: Mar. 29, 2011

(54) PHYSICAL ACTIVITY MANAGER

(75) Inventors: Chris Demetrios Karkanias, Sammamish, WA (US); Stephen Edward Hodges, Cambridge (GB)

(73) Assignee: Microsoft Corporation, Redmond, WA (US)

( * ) Notice: Subject to any disclaimer, the term of this patent is extended or adjusted under 35 U.S.C. 154(b) by 526 days.

(21) Appl. No.: 11/754,565

(22) Filed: May 29, 2007

(65) Prior Publication Data
US 2008/0300109 A1 Dec. 4, 2008

(51) Int. Cl.
*A63B 71/00* (2006.01)
(52) U.S. Cl. .............. 482/8; 482/1; 482/9; 482/901; 434/247
(58) Field of Classification Search ............ 482/1–9, 482/900–902; 434/247
See application file for complete search history.

(56) References Cited

U.S. PATENT DOCUMENTS

| | | | |
|---|---|---|---|
| 5,391,128 A * | 2/1995 | deBear | 482/4 |
| 5,721,913 A | 2/1998 | Ackroff et al. | |
| 5,890,997 A * | 4/1999 | Roth | 482/8 |
| 6,629,019 B2 | 9/2003 | Legge et al. | |
| 6,656,091 B1 * | 12/2003 | Abelbeck et al. | 482/9 |
| 7,056,265 B1 * | 6/2006 | Shea | 482/8 |
| 7,648,442 B2 * | 1/2010 | Yurich et al. | 482/1 |
| 2002/0055419 A1 * | 5/2002 | Hinnebusch | 482/8 |
| 2003/0211916 A1 * | 11/2003 | Capuano | 482/8 |
| 2007/0033069 A1 * | 2/2007 | Rao et al. | 705/2 |
| 2007/0135264 A1 * | 6/2007 | Rosenberg | 482/8 |
| 2007/0219059 A1 * | 9/2007 | Schwartz et al. | 482/8 |

FOREIGN PATENT DOCUMENTS
WO WO 2005091779 A2 10/2005

OTHER PUBLICATIONS
International Search Report and Written Opinion for PCT Application No. PCT/US2008/064817, mailed Oct. 31, 2008, 12 pages.

* cited by examiner

*Primary Examiner* — Glenn Richman
(74) *Attorney, Agent, or Firm* — Turocy & Watson, LLP

(57) ABSTRACT

A system that facilitates activity management and tracking with respect to an individual is disclosed. The innovation employs the notion of establishing a strategy to compress activity information into an identifying indicia (e.g., two-dimensional barcode) that can be processed (e.g., scanned) by a wide array of devices (e.g., mobile phone, personal data assistant). The innovation discloses a system that facilitates the ability to plan, monitor and log activity of an individual. The planning phase enables a user or third party (e.g., healthcare professional) to proactively define an exercise or activity regimen for a user. The monitoring phase enables real-time fitness and/or activity tracking of an individual. Finally, the logging phase enables a user to log the information into a fitness log that can be subsequently used in health or fitness-related assessment.

20 Claims, 15 Drawing Sheets

PHYSICAL ACTIVITY MANAGER

BACKGROUND

'Working out' often refers to an act of physical activity in an effort to promote healthy living. Today, there is an ever-growing emphasis on healthy living, and accordingly, physical activity. Generally, many people regularly 'work out' in an effort to control weight gain, build muscle mass, rehabilitate injuries, prevent injuries or even to provide an outlet for stress or social connections. For example, many professionals regularly incorporate a visit to the health club into their hectic work schedule as a way to regulate stress, keep fit while at the same time adding social aspects to their busy days. No matter the reason, working out is at the forefront for many people in today's society to live a healthier life as well as to look and feel better while doing it.

Working out, or physical exercise, most often refers to performance of some activity in order to achieve physical fitness or maintain overall good health. For instance, working out can range from anaerobic exercise to aerobic exercise. With regard to anaerobic activity, working out can include weight training or resistance training to develop or increase muscle strength. Aerobic exercise focuses on developing or increasing cardiovascular endurance and/or weight loss. In addition to anaerobic and aerobic exercise, many individuals engage in a regular routine of flexibility exercises which improve the range of motion of joints and muscles.

In addition to developing and increasing muscle strength/tone, cardiovascular endurance and flexibility, working out is often used to prevent health-related injuries and/or diseases. By way of example, a regular physical exercise routine is an important component in the prevention of some diseases such as cardiovascular disease, heart disease, diabetes, obesity, among others.

Of course, the type of physical activity and corresponding desired results may not be consistent between individuals. For example, one individual may be interested in building muscle mass (e.g., anaerobic) while another may be interested in enhancing cardiovascular endurance or weight loss (e.g., aerobic). However, a common thread of healthy living is regular physical activity whether it be anaerobic, aerobic or flexibility training. Moreover, today, some individuals are constantly 'battling the bulge' or the 'rollercoaster of weight' by trying to exercise by adhering to rigorous workout routines.

In order to be effective, most workout regimens or routines require individuals to manually record progress by journaling repetition counts, weight amounts, distances, etc. For example, weight training involves many different exercises that focus on different muscles or groups of muscles. Additionally, the amount of weight used and the number of repetitions completed dictate and yield different results. For instance, heavier weight with a lower number of repetitions tends to build muscle mass while lighter weight with an increased number of repetitions shares some of the effects of aerobic training, e.g., toning and weight loss. Thus, it is critical that a particular routine be tailored to achieve desired results. Unfortunately, oftentimes individuals do not possess the necessary knowledge to formulate an effective workout routine to achieve a desired result. Regardless of the routine, manual journaling is inherently vulnerable to mistakes or intentional manipulation.

SUMMARY

The following presents a simplified summary of the innovation in order to provide a basic understanding of some aspects of the innovation. This summary is not an extensive overview of the innovation. It is not intended to identify key/critical elements of the innovation or to delineate the scope of the innovation. Its sole purpose is to present some concepts of the innovation in a simplified form as a prelude to the more detailed description that is presented later.

The innovation disclosed and claimed herein, in one aspect thereof, comprises a system that facilitates the ability to plan, monitor and log activity of an individual. Effectively, the innovation can be broken into three phases which include a planning phase, monitoring phase and a logging phase. In aspects, each of these phases can be employed separate from the others.

The planning phase enables a user or third party (e.g., health-care professional) to proactively define an exercise or activity regimen for a user. For instance, the regimen can be defined and encoded into identifying indicia such as a bar code, magnetic strip, key fob, radio frequency identification (RFID) tag, or the like. Subsequently, this information can be automatically input into an exercise or fitness apparatus (e.g., treadmill) thereby automatically programming the desired regimen.

Another phase of the innovation is directed to monitoring activity of an individual. For example, in one scenario, a fitness facility can provide information related to an individual that identifies completed exercise or activity. This information can be automatically generated by individual fitness apparatus or from a centralized location and can be communicated in the form of an Internet link, barcode or other suitable identifying indicia.

In the logging phase, a user can log the information into a fitness log that can be subsequently used in health or fitness-related assessment. In a barcode scenario, the innovation employs the notion of establishing a strategy to compress activity information into a two-dimensional form (e.g., barcode) that can be scanned by a wide array of devices (e.g., mobile phone, personal data assistant). In operation, the ability to scan this information into a health strategies system enhances the usability while minimizing the effort needed to manually inject information into a fitness or activity tracking system. Moreover, because there is little or no human input, error is greatly reduced.

In yet another aspect thereof, artificial intelligence and/or machine learning and reasoning logic is provided that employs a probabilistic and/or statistical-based analysis to prognose or infer an action that a user desires to be automatically performed.

To the accomplishment of the foregoing and related ends, certain illustrative aspects of the innovation are described herein in connection with the following description and the annexed drawings. These aspects are indicative, however, of but a few of the various ways in which the principles of the innovation can be employed and the subject innovation is intended to include all such aspects and their equivalents. Other advantages and novel features of the innovation will become apparent from the following detailed description of the innovation when considered in conjunction with the drawings.

DETAILED DESCRIPTION

Figure 1:
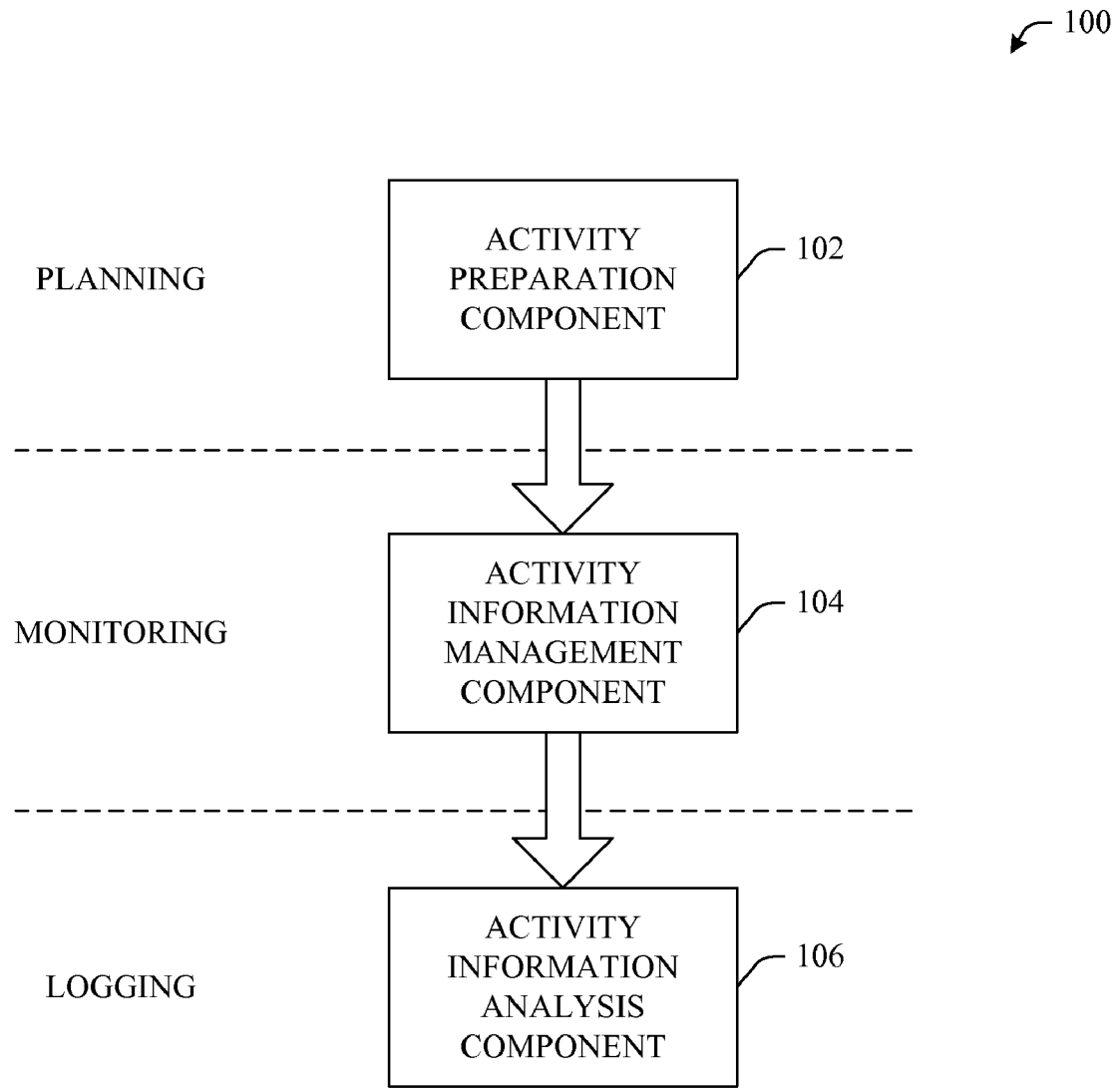
FIG. 1 illustrates a system that facilitates activity management via planning, monitoring and logging phases in accordance with an aspect of the innovation.

The innovation is now described with reference to the drawings, wherein like reference numerals are used to refer to like elements throughout. In the following description, for purposes of explanation, numerous specific details are set forth in order to provide a thorough understanding of the subject innovation. It may be evident, however, that the innovation can be practiced without these specific details. In other instances, well-known structures and devices are shown in block diagram form in order to facilitate describing the innovation.

As used in this application, the terms "component" and "system" are intended to refer to a computer-related entity, either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution, and a component can be localized on one computer and/or distributed between two or more computers.

As used herein, the term to "infer" or "inference" refer generally to the process of reasoning about or inferring states of the system, environment, and/or user from a set of observations as captured via events and/or data. Inference can be employed to identify a specific context or action, or can generate a probability distribution over states, for example. The inference can be probabilistic—that is, the computation of a probability distribution over states of interest based on a consideration of data and events. Inference can also refer to techniques employed for composing higher-level events from a set of events and/or data. Such inference results in the construction of new events or actions from a set of observed events and/or stored event data, whether or not the events are correlated in close temporal proximity, and whether the events and data come from one or several event and data sources.

Referring initially to the drawings, FIG. 1 illustrates a system 100 that assists in managing, tracking and logging physical activity of an individual. Generally, system 100 includes an activity preparation component 102, an activity information management component 104 and an activity information analysis component 106, which, as illustrated, represent the planning, monitoring and logging phases respectively. Each of these components and phases will be described in greater detail below with reference to the figures that follow.

The activity preparation component 102 enables a healthcare or physical activity regimen to be programmed, preprogrammed or otherwise automatically configured. In a particular example, this regimen can be formulated by a health-care professional (e.g., physical therapist, personal trainer) in efforts to achieve a particular goal or merely to promote healthy living. Once a regimen or routine is formulated, it can be incorporated into an identifying indicia (e.g., barcode, radio frequency identification tag (RFID), magnetic strip, memory stick/fob).

Once the regimen is incorporated into identifying indicia, the particulars of the regimen can be communicated to most any type of suitable of exercise apparatus or activity device. For instance, a treadmill can receive the preprogrammed or prescribed routine and thereafter automatically set parameters such as pace, inclination, distance, etc., in order to achieve such a routine. It will be understood that the variations of programming activity related information are endless. Thus, this specification is to include all examples and/or permutations conceivable. In other words, the functionality of programming, preprogramming or inferring a routine and transferring that routine to appropriate equipment (e.g., treadmills, haptic braces) is to be included within the scope of this disclosure.

With continued reference to FIG. 1, the system 100 can include an activity information management component 102 that generates actual activity information related to exercise and/or activity of an individual. In other words, as an individual engages in physical activity, the management component 104 can dynamically monitor and, if appropriate, adjust the regimen to conform to a desired goal. For example, suppose a regimen includes a defined number of repetitions on a particular device, here, if a user is unwilling or unable to complete the defined repetitions, the management component 104 can automatically adjust the routine so as to 'make up' the amount of exercise at a later point in the routine. For instance, if a defined number of calories are to be burned, the management component 104 can increase repetitions and/or other parameters with regard to other devices/exercises so as to compensate for the deviation of the regimen.

An activity information analysis component 104 can be employed to automatically access the recorded activity information. In aspects, the activity information can be logged by the service (e.g., health club), client, in a cloud, or combination thereof. These aspects will be better understood upon a review of the figures that follow.

The system 100 employs the notion of establishing a strategy to compress activity information into a transferable form (e.g., two-dimensional form (e.g., barcode)) that can be understood (e.g., scanned) by a wide array of devices. In operation, the ability to accept (e.g., scan) this information into health strategies systems enhances the usability of the information while minimizing the effort needed to inject the information into the system 100. As described above, the preprogrammed information can be injected into equipment to manage operation to promote achieving a particular goal.

By way of example, at a health club (e.g., service), a user can perform an exercise regimen, either preprogrammed (e.g., via activity preparation component 102) or as desired (e.g., on-the-fly). Regardless if preprogrammed or not, a record can be printed to include a bar code or set of bar codes that identify the individual activities completed. Once scanned by an individual (e.g., client), the information can be stored locally within a scanning device (e.g., activity information analysis component 104) to be uploaded or transferred at a later time (e.g., when docked to a network). In other aspects, the information can be immediately uploaded to an on-line or cloud-based remote network.

In other aspects, the information can be stored within the particular exercise device and/or onto a memory stick/fob, membership card magnetic strip, RFID tag, or the like. It is to be understood that this information can be stored in most any suitable manner that links or associates an individual to particular activities completed (or not completed as the case may be).

It is to be appreciated that this coded information can include repetitions completed, distance traveled, inclination rates, speed/velocity rates, weight amounts, etc. which can be uploaded and stored for later analysis with respect to activity, exercise or progress reconciliations. Alternatively, the code can merely identify the exercises completed whereby specific activity-based characteristics (e.g., calories burned, progress reports, etc.) can be gathered using a query of a cloud (e.g., Internet) or other data storage mechanism. In either instance, the transfer of activity information can be accurate and seamless to a user thereby enhancing the usability of the activity-based system 100. Ultimately, this information can be rendered, stored and/or employed in the context of a specific health or fitness-based record. Thus, activity and exercise can be evaluated and/or regulated within context related to progress, physical state, mental state (e.g., mood), time of day, etc.

Aspects can employ 'cloud' or network based data and/or communication. In one embodiment, the physical activity manager can 'live' in the service cloud. As well as providing a mechanism to enter and maintain a regimen of activity (e.g., via a web interface), the regimen to be printed by a user (e.g., as a barcode of some kind), or possibly to be automatically downloaded to a piece of exercise or activity equipment. Users could also print out other user statistics. For example, a user could print out a third party's (e.g., friend's) data. This data could be scanned or entered into a machine in order to race or compete against them. Additionally, high-score tables, statistics of performance trends or the like could be maintained and/or accessed for groups of users.

The printed barcode concept described supra could work in reverse, for instance, at the end of a workout (on a single exercise machine or across several machines) a user could get a print out of performance that could be maintained for future use. In aspects, this print out could be scanned into a computer at home (e.g., using a web cam or camera phone) or kept and used for the next visit to the gym. The former would enable a user to keep track of performance over time, and could be used to modify profile statistics, which could be printed out for next time. The latter could be used so that next time the user visits the gym, a comparison with the previous performance can be easily obtained.

In other embodiments, the innovation enables the ability to create, organise and maintain teams using the 'cloud' infrastructure. For instance, users can be dynamically associated into teams based upon ability, demographics, etc. The user could even have scheduled workouts where team members agree to exercise at the same time even though they may be in different physical locations. This could provide a form of motivation, and teams could even have competition fixtures.

The cloud could also have an interface to various business entities. For example, physicians, drug companies and health insurers may desire to access the exercise data for application to a specific industry. Other businesses such as consumer goods manufacturers might also want to access data within the cloud for target advertising or the like. In one embodiment, users might earn money-off coupons (which could be printed as barcodes) as rewards for certain activities. It is to be understood and appreciated that there can also be an interesting business model where gym membership fees are can be reduced if based upon frequency of gym use, performance levels or the like.

Figure 2:
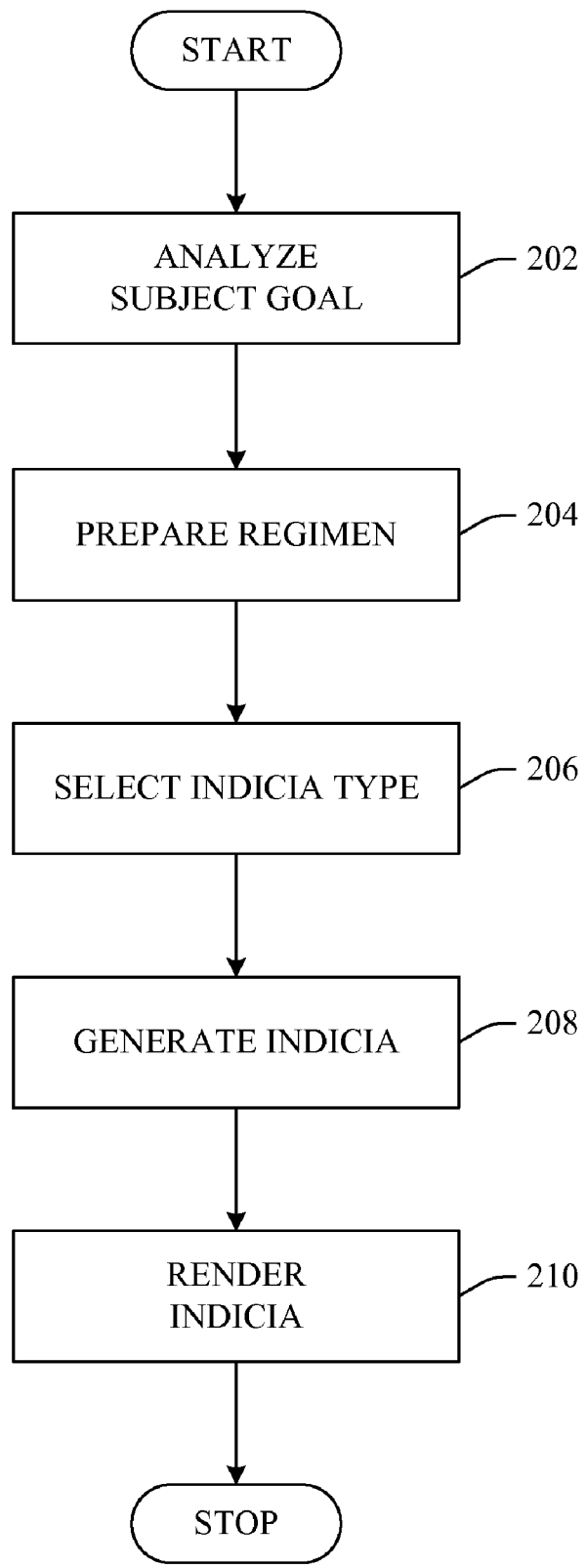
FIG. 2 illustrates an example flow chart of procedures of a planning phase in accordance with an aspect of the innovation.

FIG. 2 illustrates a methodology of planning an exercise or activity regimen in accordance with an aspect of the innovation. Generally, the methodology of FIG. 2 enables a particular routine to be incorporated into a code or other identifying indicia such that activity can be managed and/or regulated. As described above, a health-care professional such as a physical therapist or sports trainer can formulate a regimen which can be planned to achieve a particular goal. For example, the goal can be weight loss, weight management, muscle development, rehabilitation, etc. No matter the reason, the regimen can be incorporated into a transferable form (e.g., identifying indicia) which can be employed to regulate or manage activity as desired.

While, for purposes of simplicity of explanation, the one or more methodologies shown herein, e.g., in the form of a flow chart, are shown and described as a series of acts, it is to be understood and appreciated that the subject innovation is not limited by the order of acts, as some acts may, in accordance with the innovation, occur in a different order and/or concurrently with other acts from that shown and described herein. For example, those skilled in the art will understand and appreciate that a methodology could alternatively be represented as a series of interrelated states or events, such as in a state diagram. Moreover, not all illustrated acts may be required to implement a methodology in accordance with the innovation.

At 202 a subject goal can be analyzed to initiate the process of planning a particular work out or activity regimen. For example, a goal can range from weight loss to weight gain or from joint/muscle rehabilitation to strength training. It is to be understood that most any activity-related goal can be addressed in accordance with aspects of the innovation.

A regimen can be prepared at 204. For instance, if weight loss is the desired goal, a regimen of aerobic activity can be formulated. Similarly, if strength training is desired, a regimen of anaerobic activity can be devised. Essentially, at 204, the regimen can be prepared to address a specific goal.

An indicia type can be selected at 206 by which the regimen can be incorporated. For instance, a barcode can be selected to be the medium to incorporate the regimen. The indicia can be generated at 208, or example, a barcode that incorporates a regimen can be generated. In other examples, the regimen can be incorporated into an RFID tag, magnetic strip, memory stick/fob, etc. without departing from the spirit and scope of the disclosure and claims appended hereto.

At 210, the indicia can be rendered thereby transferring the incorporated regimen as desired. For instance, a mobile device (e.g., cell phone) can be employed to scan a barcode thereby transferring the regimen into the memory of the device. Thus, continuing with this example, the regimen can be automatically (wirelessly or wired) to a particular exercise device (e.g., treadmill, haptic brace) in order to manage operation of the apparatus. It will be appreciated that other examples exist which are to be included within the scope of this specification and claims appended hereto.

Figure 3:
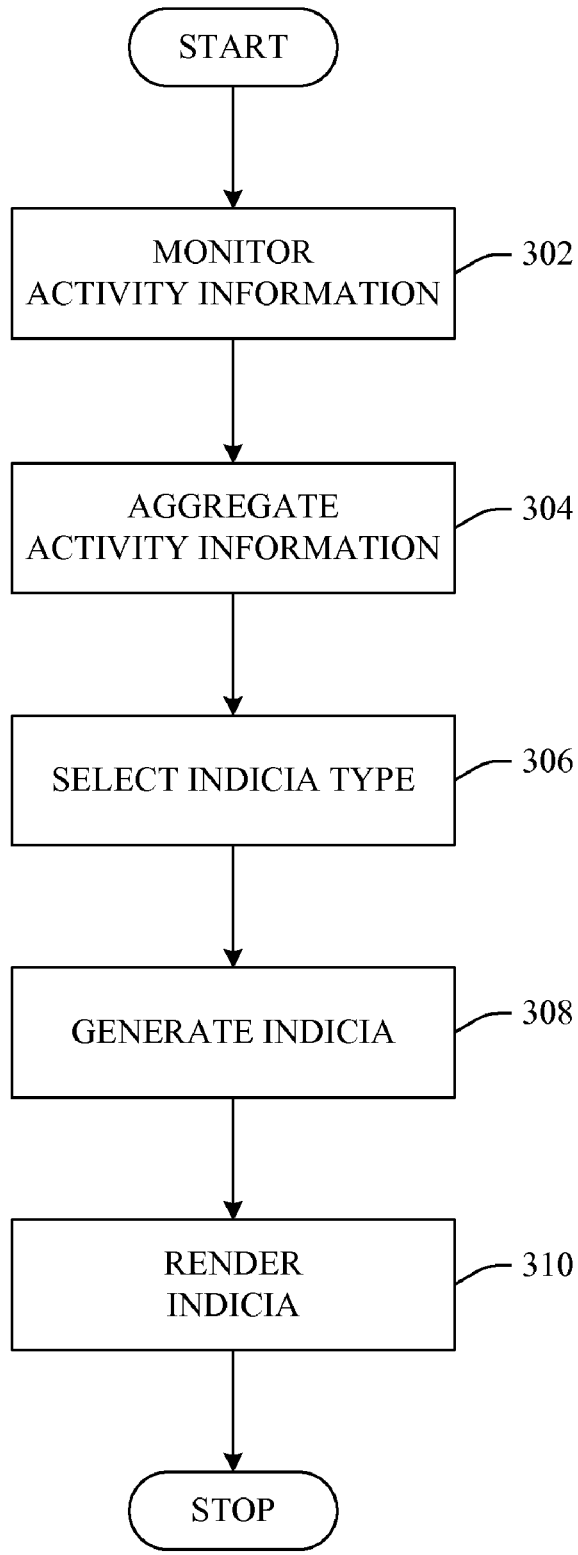
FIG. 3 illustrates an example flow chart of procedures of a monitoring phase in accordance with an aspect of the innovation.

FIG. 3 illustrates a methodology of monitoring activity information in accordance with an aspect of the innovation. Essentially, in an aspect, this methodology can be viewed as acts of the monitoring phase of the system 100 of FIG. 1. However, while many of the examples described herein are directed to a health club or fitness scenarios, it is to be understood that the information can be gathered and incorporated into an indicia or code (e.g., barcode) by other means in alternative scenarios. For instance, magazines and other specialty fitness sources (e.g., websites) can incorporate activity or exercise information into a barcode (or other identifying indicia) which can be accessed by a user. Thus, when an individual desires to work out, the code can be input or analyzed (e.g., scanned) in order to automatically calibrate a particular device (as described in FIG. 2 supra).

Referring now to FIG. 3, at 302, activity information can be monitored and aggregated at 304, for example, number of repetitions, amount of weight, distance traveled, etc. In examples, fitness apparatuses can be equipped with sensory technologies to monitor and aggregate the information. In other aspects, haptic braces and/or sensory technologies can be applied to an individual in order to capture the activity information. This activity information can be used for most any purpose, for example, handicapping as a function of performance. The 'handicap' can be used to 'level the playing field' when competing (e.g., racing) another user in either the same physical space or via a virtual or cloud-based connection. The haptic brace can not only be used for 'handicapping', but also as a monitor of the 'quality' of exercise in terms of how well the user is moving their joints and as an alarm if the user is exercising in a way that is likely to cause injury or long-term problems.

An indicia type can be selected at 306. By way of example, a barcode can be used as indicia to encode information relating to activity and/or fitness. As will be understood, a 'barcode' is a machine-readable representation that uses dark ink on a light substrate to create high and low reflectance which, when scanned, can be converted into binary 1's and 0's. While original barcodes stored data in the widths and spacing of parallel lines, today, barcodes can employ patterns of dots, concentric circles, etc.

Traditionally, barcode encoding schemes represented only numbers; however, newer symbologies add new characters such as the uppercase alphabet to the complete ASCII character set and beyond. The drive to encode more information in combination with the space requirements of simple barcodes led to the development of 'matrix codes' (a type of two-dimensional (2D) barcode), which, contrary to their name, do not consist of bars but rather a grid of square cells. Similarly, 'stacked barcodes' are a compromise between true 2D barcodes and linear codes, and are formed by taking a traditional linear symbology and placing it in an envelope that allows multiple rows.

At 308, the indicia (e.g., barcode) can be generated. While the aforementioned example addresses barcodes as the indicia, it is to be understood that other examples employ other suitable indicia (e.g., matrix codes, hyperlinks, universal resource locator (URL), magnetic strips, RFID tags) without departing from the spirit and scope of this specification and claims appended hereto. At 308, the indicia can be rendered (e.g., printed, displayed, transmitted). Referring again to the system 100 of FIG. 1, here the indicia can be rendered from the monitoring phase to the logging phase by being embedded into a barcode, transferred into a fitness club membership card, or the like.

Figure 4:
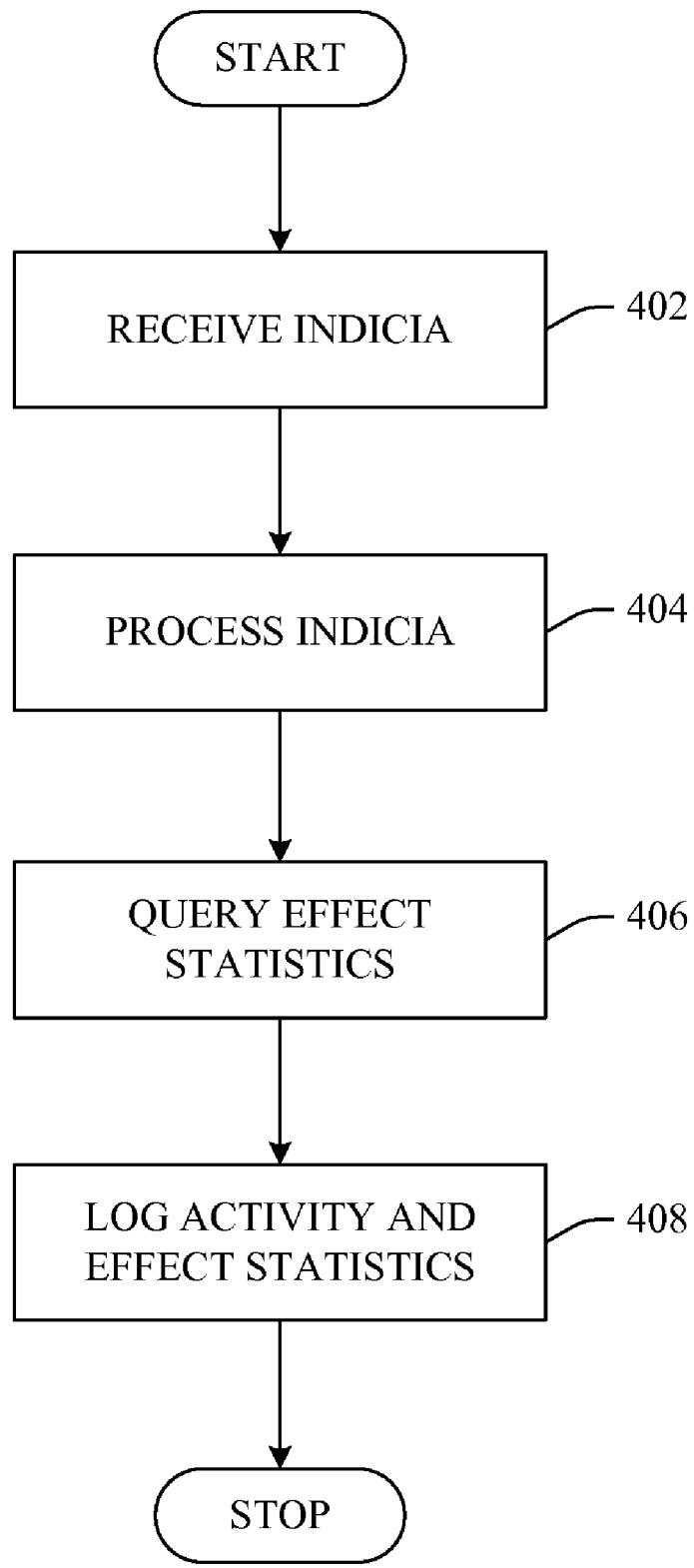
FIG. 4 illustrates an example flow chart of procedures of a logging phase in accordance with an aspect of the innovation.

Turning now to FIG. 4, there is illustrated a methodology of interpreting indicia or logging information in accordance with the innovation. At 402, the indicia can be received. For instance, a barcode which is printed directly from an exercise apparatus as indicated in the methodology described in FIG. 3 can be received and processed at 404. Here, at 404, processing can refer to any act of interpreting the indicia. For instance, the act in 404 can refer to an act of scanning the barcode in order to determine information encoded therein. In another embodiment, for example a URL, the act of processing indicia at 404 can refer to an act of accessing a particular website designated by the URL in order to access exercise and/or activity information.

At 406, a query can be employed to establish physiological statistics related to the identified information. For example, suppose the barcode reveals that a specific distance was traveled on a treadmill or stair stepper. Here, at 406, physiological statistics (e.g., calories burned) can be gathered by way of a data store, cloud, etc. to further establish the effects on a subject based upon the amount of activity together with profile information related to the individual (e.g., height, weight, age). In alternative aspects, if possible, the actual statistics can be incorporated into the indicia by the respective recording device. Additionally, it will be understood that other information related to the activity information can be queried for, analyzed and logged at 408.

Once the information is logged at 408, it can be employed for most any purpose desired. For instance, the information can be provided to a health-care professional such as a physical therapist, strength coach, cardiovascular physician or general practice physician in order to assess adherence to a specified or prescribed regimen. In operation, the information can be logged locally and subsequently transferred to a server or other target upon 'docking' (e.g., wired or wireless). In a specific example, the information can be stored locally on a mobile device and transferred via an opportunistic network upon detection of an available connection. In this example, a user can visit an exercise facility, workout and receive the activity information directly onto their mobile device. When they arrive home, the mobile device can automatically 'dock' to a home network and the information can subsequently be transferred and compiled with other health-related information within the home network. Thus, an automatic activity journal can be established seamlessly without intervention by the user.

Figure 5C:
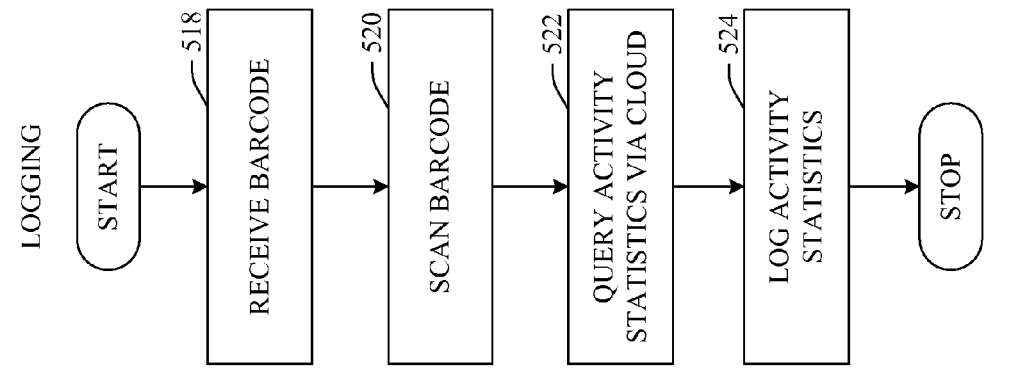
FIG. 5C illustrates an example flow chart of procedures that facilitate process of the barcode in accordance with the logging phase of the innovation.
Figure 5B:
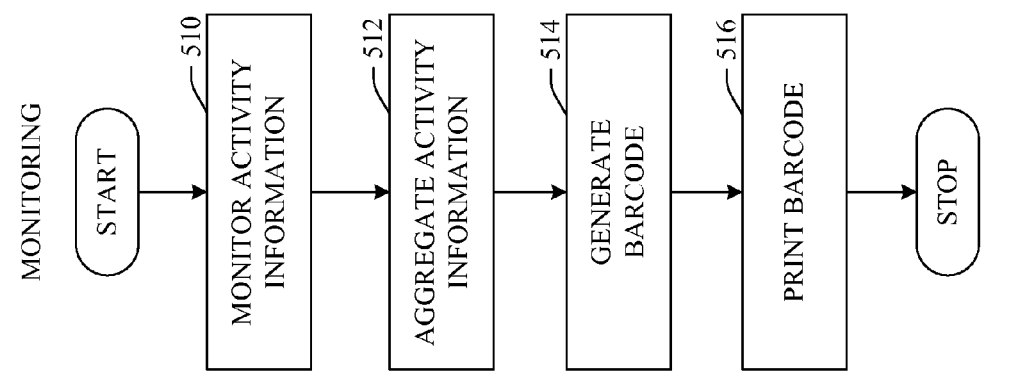
FIG. 5B illustrates an example flow chart of procedures that facilitate generating a barcode that encodes activity information in accordance with a monitoring phase of the innovation.
Figure 5A:
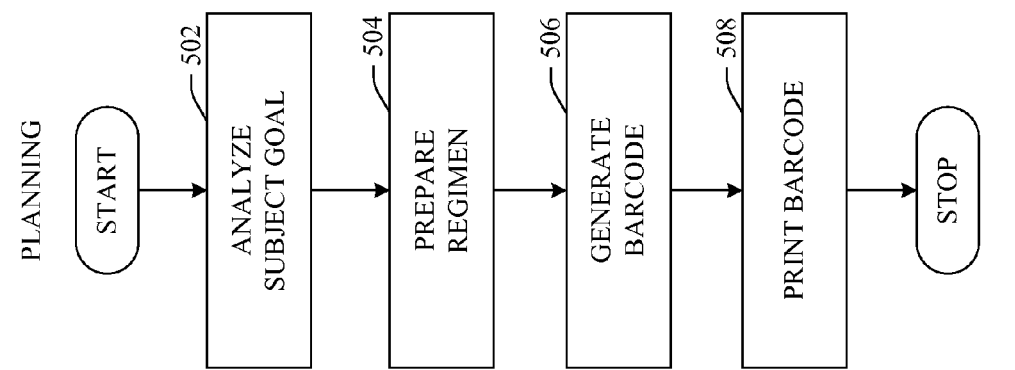
FIG. 5A illustrates an example flow chart of procedures that facilitate generating a barcode with regard to a planning phase of the innovation.

FIGS. 5A, 5B and 5C illustrate methodologies of the planning, monitoring and logging phases respectively in accordance with aspects of the innovation. As stated above, while these methodologies employ barcodes to embody activity information, it is to be understood that most any suitable indicia, symbol, identifier or transferable medium can be employed to either incorporate the information or to point to a source where the information can be obtained. For instance, a URL can be provided to navigate to a third party service in a cloud or to the originating source (e.g., health club) where specific activity information can be obtained.

Referring first to FIG. 5A, at 502, a subject goal can be analyzed. Here, a goal can be evaluated as a function of physiological characteristics of an individual. As well, the goal can be evaluated as a function of available facilities, e.g., treadmills and other exercise apparatuses. Still further, other contextual factors can be considered when analyzing the goal at 502. For example, nutritional intake, previous and expected activity events, sleep habits, mental state (e.g., mood), etc. can be evaluated and incorporated into a regimen at 504.

Here, at 504, a regimen can be formulated in view of the anticipated goal. While FIG. 5A anticipates pre-planning of a regimen, it is to be understood that other aspects of the innovation are directed to ad hoc monitoring and logging of activity information generally. In other words, the three phases are shown in FIGS. 5A, 5B and 5C merely to add perspective to the innovation and not to limit the functionality in any way.

At 506, a barcode can be generated to incorporate the parameters and/or specifics of the regimen. As described above, this information can be encoded into most any suitable indicia without departing from the spirit and/or scope of the innovation. In the case of a barcode, at 508, the barcode can be printed and given to an individual. Here, the individual can employ the barcode to automatically calibrate machines and apparatuses in accordance with the regimen. Effectively, this calibration can establish a baseline by which conformance and/or deviation can be established as a function of a particular regimen.

Referring next to FIG. 5B, at 510, activity information can be monitored and aggregated at 512. By way of example, during or after a person exercises, information can be monitored and aggregated. In a specific example, information related to type of exercise, parameters (e.g., repetitions, distance, etc.) can be aggregated. This information can include most any characteristics including, but not limited to, elapsed time, distance traveled, amount of weight, number of repetitions, physiological effects, etc. By way of further example, an individual can be equipped with physiological sensors which can record effects before, during and after exercising.

A barcode which incorporates the activity (and physiological) information can be generated at 514. As described, above a 2D barcode can be generated to incorporate the information. This 2D barcode can be printed at 516 directly from each apparatus or from a centralized location. Alternatively, the information can be automatically transferred (e.g., via an opportunistic network connection) into the individual's mobile device (e.g., cell phone, smartphone, personal digital assistant).

In addition to, or in place of, printing the barcode, the bar code (or other indicia) can be electronically transferred to a user by way of electronic protocols. By way of example, and not limitation, the information can be transferred via email, instant message (IM), SMS (short message service (text message)), etc. Once sent, this information can be automatically received and interpreted as described with reference to FIG. 5C.

Turning now to FIG. 5C, a methodology of interpreting the barcode and logging the activity information is shown. At 518, the barcode is received. As described supra, the barcode can be directly accessed from each exercise apparatus or from a centralized location. Alternatively, the information can be sent via electronic protocol (e.g., email, IM, SMS). In the case of a barcode, at 520, the barcode can be scanned to interpret the information encoded therein.

At 522, additional activity and physiological statistics can be queried by way of a cloud or other network service. For instance, the receiving device can automatically employ a search engine to query the Internet (or other source) to obtain specific or additional activity and/or physiological information related to the information encoded within the barcode. In other words, if the barcode merely includes exercise statistics, supplemental information (e.g., calories burned) can be obtained from the Internet.

At 524, the information can be logged into a health-related journal of activity information. It is to be understood that the log can be used for most any purpose desired. In one example, the log can be used merely to track exercise patterns for fitness management. In another example, the log can be used for a specific weight management program. Still further, the log can be used to assist in rehabilitation of an individual.

Essentially, the activity information tracking functionality of the innovation enables patterns of activity (e.g., exercise) to be recorded in a flexible manner. From an outbound perspective, the functionality enables actions to be recorded. Similarly, from an inbound perspective, the functionality enables actions to be controlled, for example, by specifying what exercises are to be performed. As described above, the indicium (e.g., barcode) represents a mechanism that defines a pattern of activity in an offline manner.

In accordance with the features functions and benefits of the innovation, there are at least three scenarios that can be employed in connection with providing a printed code, for example a 2D barcode or URL. In a first scenario, a user can employ a scanning device, for example within a home network or on a mobile device, to scan the code thereby retrieving information encoded therein. In a second scenario, rather than encoding the detailed information within a barcode, the service could simply provide a third party URL which can be used to retrieve the information. Here, a third party can be engaged thus taking burden away from both the service as well as the client with regard to maintaining the information or employing additional hardware devices respectively. In yet a third scenario, the service itself can host a mechanism which maintains the activity information. In this scenario, rather than the client connecting to a third party, here, they would essentially connect directly to the health club to access and/or retrieve the information. In this scenario, a suitable code and identifying parameters can be supplied to the user in order to identify the correct information.

Figure 6:
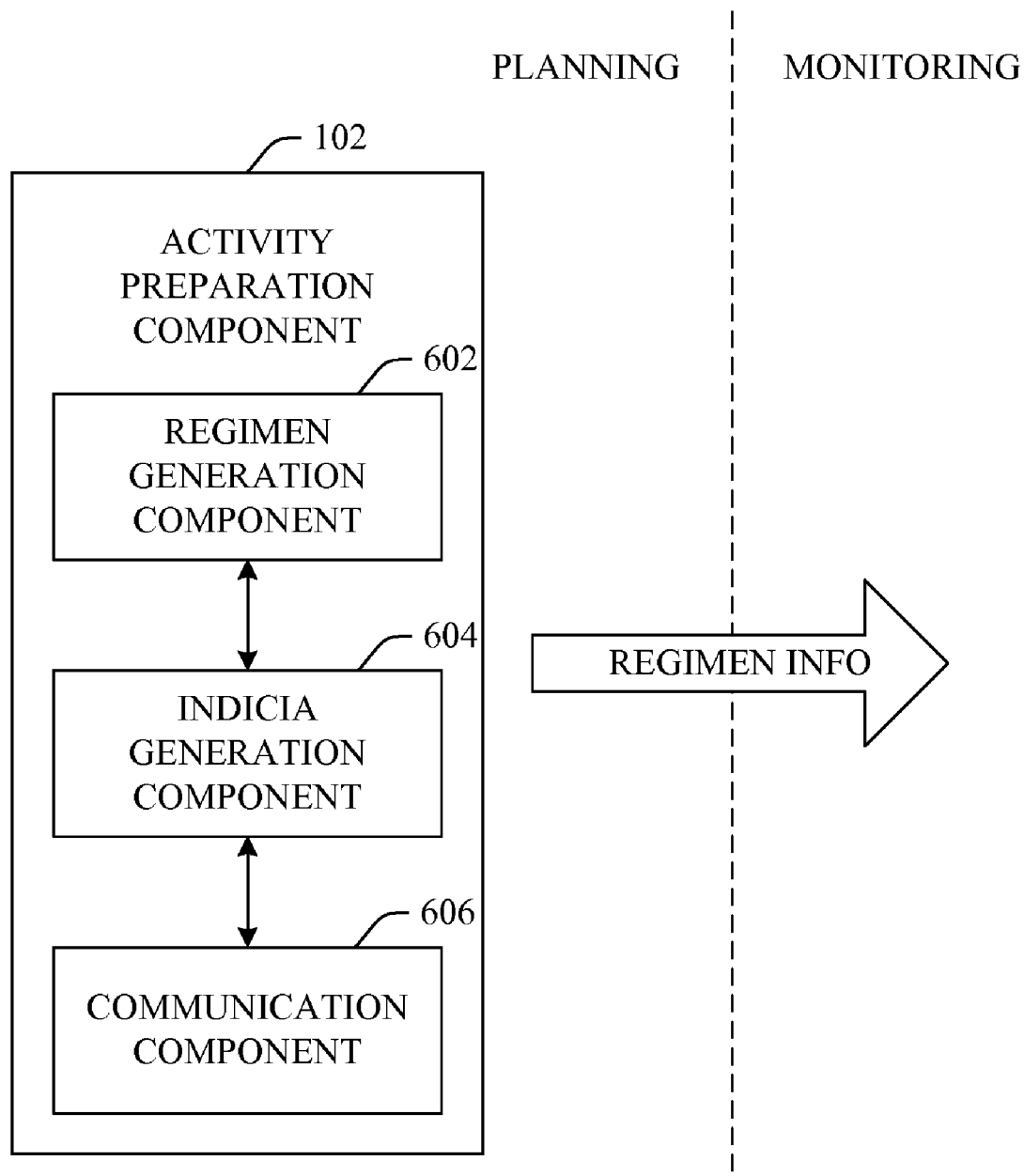
FIG. 6 illustrates an exemplary block diagram of an activity preparation component in accordance with an aspect of the innovation.

Referring now to FIG. 6, a block diagram of an example activity preparation component 102 is shown. Effectively, this activity preparation component 102 enables an activity regimen to be established, incorporated into indicia and communicated to a user (or apparatus) in accordance with the innovation. As shown, the activity preparation component 102 can include a regimen generation component 602, an indicia generation component 604 and a communication component 606.

The regimen generation component 602 can facilitate compilation of an exercise or activity regimen that addresses a particular goal, or set of goals. For instance, if a user is interested in losing weight, the regimen generation component 602 can establish specific exercises to achieve this stated goal. In doing so, the component 602 can consider characteristics about the individual (e.g., physiological parameters) as well as information related to availability of exercise apparatuses (e.g., treadmills, elliptical machines).

An indicia generation component 604 can be employed to incorporate the information into a suitable transferable indicia or medium, such as a barcode. In other examples, the regimen can be incorporated into an RFID tag, a magnetic strip, a memory stick/fob, or the like. A communication component 606 can be employed to communicate the regimen to a particular apparatus. For instance, in the case of a barcode, a scanner can be employed to automatically enter the information into particular apparatuses. Similarly, card readers, RFID tag readers, memory stick/fob readers, etc. can be employed to transfer the information into a particular apparatus. Once transferred, the apparatus can be automatically calibrated in accordance with achieving or attempting to achieve a specified goal.

Figure 7:
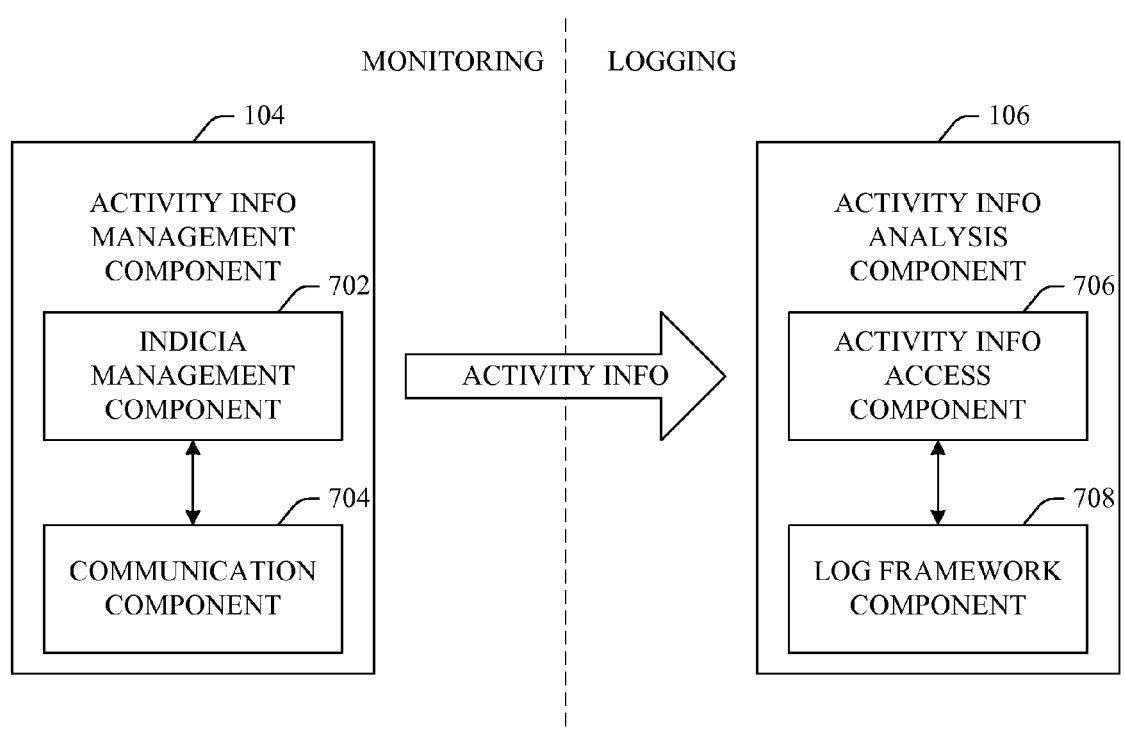
FIG. 7 illustrates an example block diagram of components and communication between the monitoring and logging phases of the innovation.

Referring now to FIG. 7, an alternative block diagram monitoring and tracking phases of the system 100 of FIG. 1 is shown. As illustrated, the activity information management component 104 can include an indicia management component 702 and a communication component 704. Similarly, the activity information analysis component 106 can include an activity information access component 706 and a log framework component 708. Each of these sub-components will be described in greater detail infra.

The indicia management component 702 can select the type of indicia or identifier (e.g., barcode) for which to embody the activity information. Further, the indicia management component 702 can aggregate appropriate information (e.g., calories burned, physiological effects, progress) and subsequently generate appropriate indicia to communicate the information.

The communication component 704 can be employed to actually communicate the information. In one example, communication can be of the form of printing the barcode directly from an exercise apparatus. In other examples, information can be electronically transferred to a mobile device using most any wired or wireless protocol (e.g., Bluetooth, infrared, Wi-Fi). Still further, a URL or other pointer can be employed to convey sufficient information to enable a user to locate the monitored information in a cloud or other storage location. It will be understood that the information can be managed by an originating service or a third-party service provider.

Figure 8:
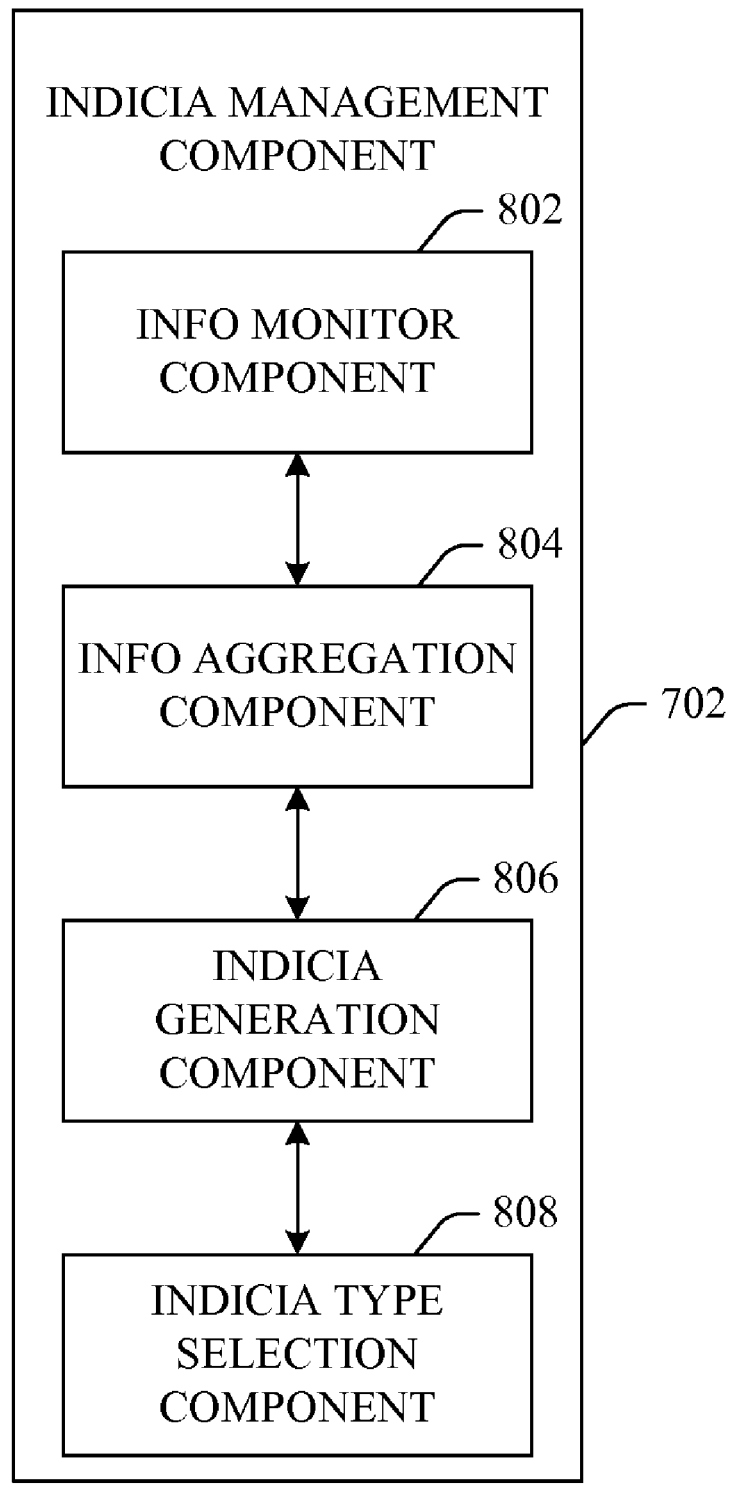
FIG. 8 illustrates a block diagram of an indicia management component that establishes identifying indicia in accordance with an aspect of the innovation.

Turning now to FIG. 8, an example block diagram of an indicia management component 702 is shown. Generally, the component 702 can include an information monitor component 802, an information aggregation component 804, an indicia generation component 806 and an indicia type selection component 808. In operation, the information monitor and aggregation components, 802 and 804, can facilitate gathering the information that is to be incorporated and communicated. For instance, the components 802, 804 can gather information relating to all exercises and/or activity of a user. Exercise apparatuses can be equipped with sensory technologies by which information can be collected or captured. Additionally, in other examples, information can be retrieved from haptic brace technologies. Overall, this information can be gathered in most any suitable manner, for example, by integrating into a workout club facility computer system that tracks operation of apparatus for safety and maintenance purposes. Additionally, a user can manually enter exercise or activity information into the components 802, 804.

The indicia type selection component 808 can be employed to determine an appropriate manner by which to convey the information. For instance, if a hardcopy record is to be printed, it can be possible to select a barcode which can be printed by each individual apparatus (or from a centralized location). In other examples, the information can be conveyed electronically via email, IM, SMS, or the like.

Figure 9:
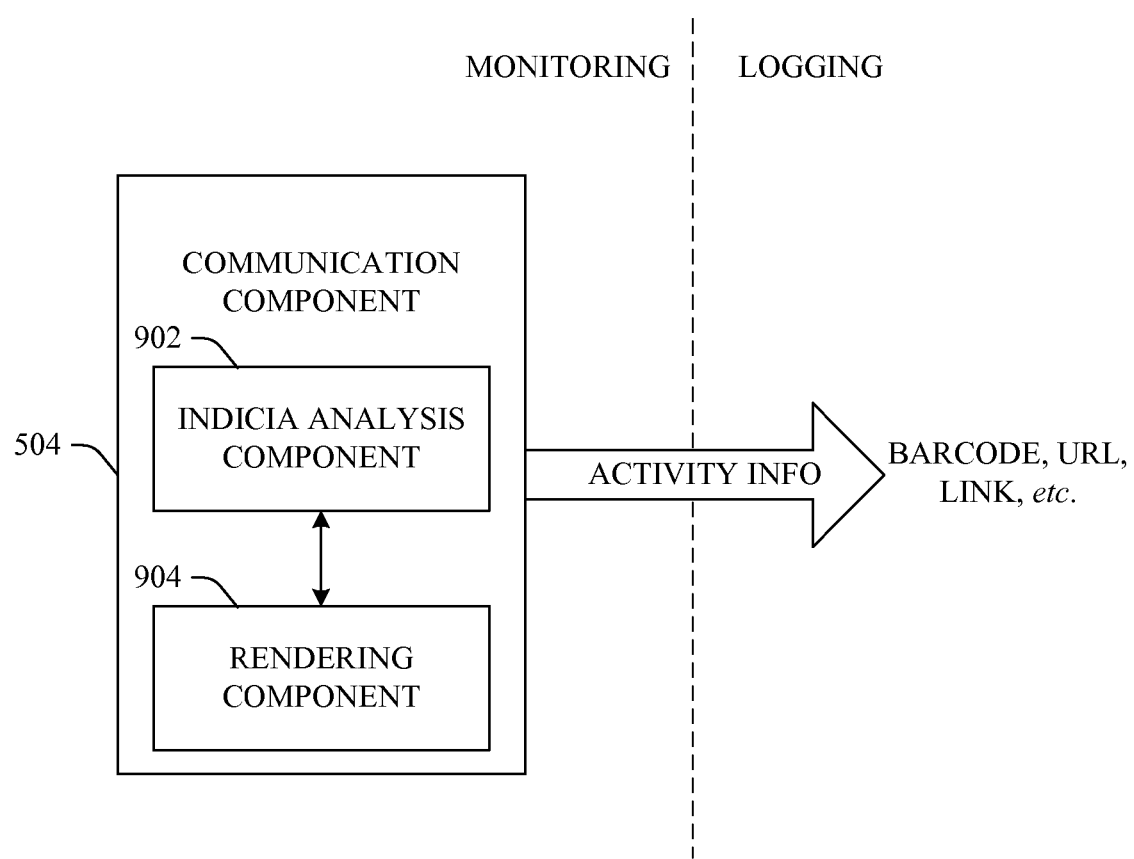
FIG. 9 illustrates a block diagram of a communication component that renders identifying indicia to a client in accordance with an aspect of the innovation.

The indicia generation component 806 can be employed to establish the means to convey the information. In other words, the generation component 806 can combine the aggregated information into the selected indicia type thereby enabling communication to a user. FIG. 9 illustrates an example communication component 704 that is capable of effectuating the transfer to a user.

Referring to FIG. 9, the communication component 704 can include an indicia analysis component 902 and a rendering component 904. In operation, the analysis component 902 can establish the type of indicia used (e.g., barcode, URL). The rendering component 904 can select an appropriate mechanism by which to render the information to a target location (e.g., user, device, application).

Figure 10:
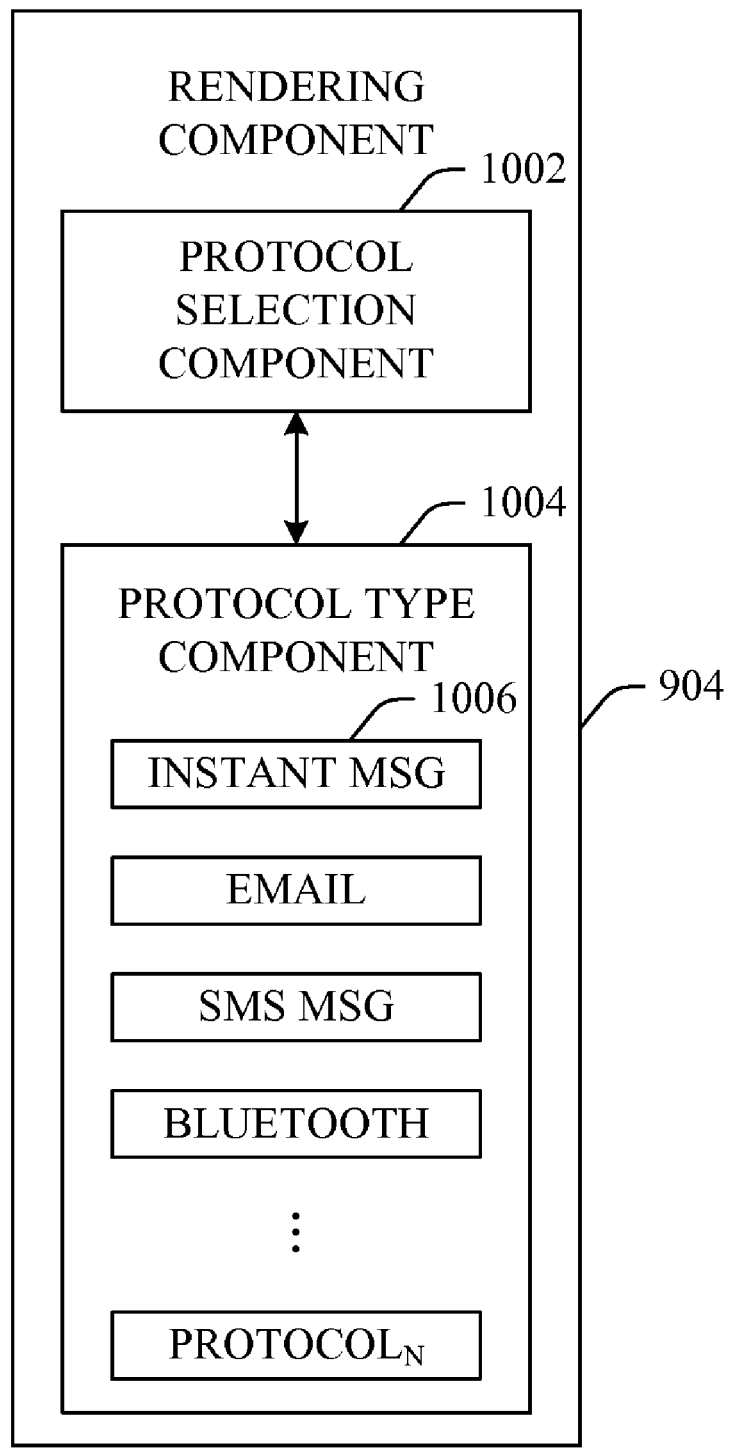
FIG. 10 illustrates a block diagram of a rendering component that facilitates selection of an appropriate protocol to transfer identifying indicia to a client in accordance with an aspect of the innovation.

FIG. 10 illustrates an example rendering component 904 in accordance with an aspect of the innovation. Essentially, the rendering component 904 can include a protocol selection component 1002 and a protocol type component 1004. In use, the protocol selection component 1002 can select one or more communication protocols (1006) from within the protocol type component 1004. Effectively, the protocol type component 1004 can maintain a list of 1 to N available protocol types, were N is an integer. As illustrated, the protocol type component 1004 can include protocol information associated with, but not limited to, IM, email, SMS message, wireless transfer (e.g., Bluetooth), or the like. Once an appropriate communication protocol, or group of protocols is selected, the indicia information can be conveyed to a target location (e.g., athlete, patient).

Figure 11:
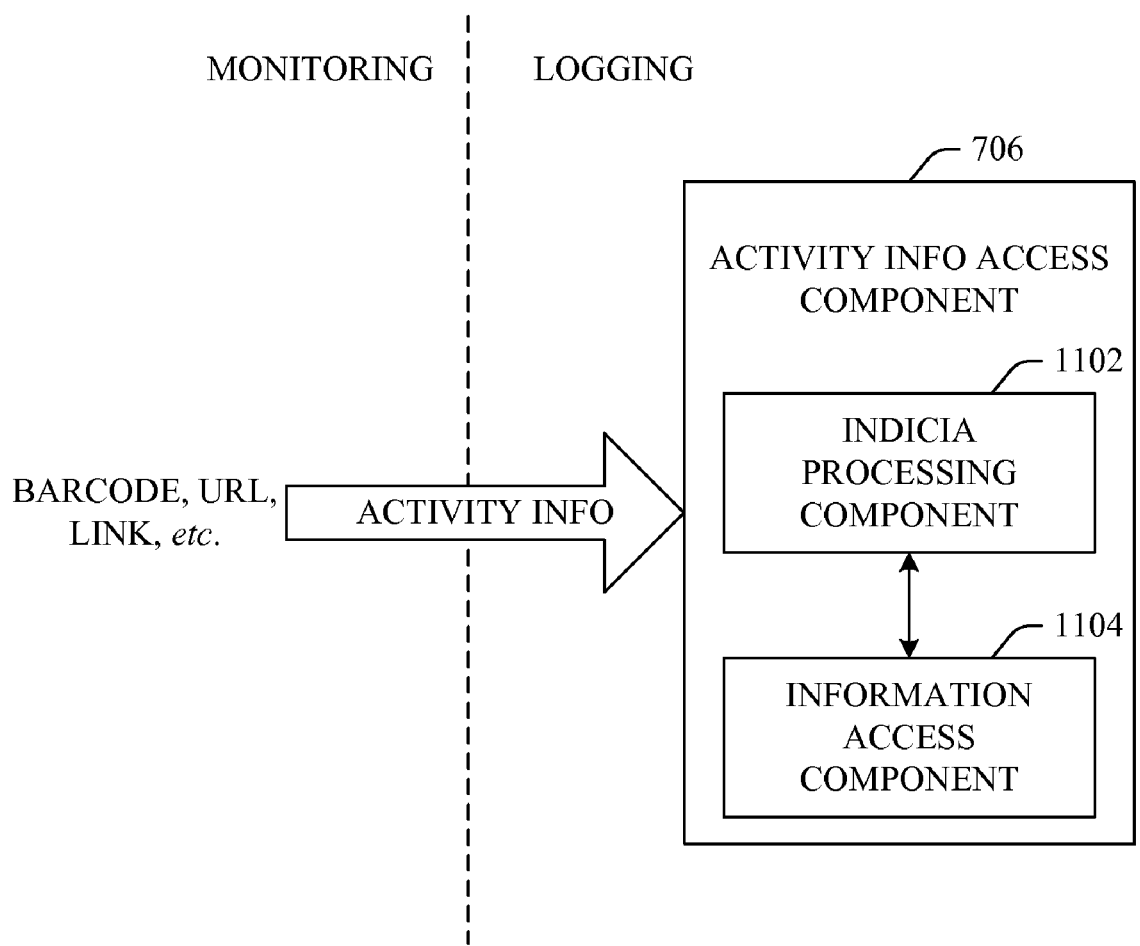
FIG. 11 illustrates a block diagram of an activity information access component that facilitates processing identifying indicia in accordance with an aspect of the innovation.

Referring now to FIG. 11, an example activity information access component 706 is shown. Generally, the access component 706 can include indicia processing component 1102 and an information access component 1104. In one example, the activity information access component 706 can be a scanner and associated logic such that a barcode provided by a service (e.g., health club facility) can be scanned to gain access to the information encoded therein.

Essentially, the indicia processing component 1102 is illustrative of a means to decipher or gain access to the code. As in the above example, the indicia processing component 1102 can be representative of a scanner. In another example, e.g., URL scenario, the processing component 1102 can be representative of a browser such that information can be accessed from a cloud or other suitable storage mechanism.

The information access component 1104 can be employed to retrieve supplemental or detailed information related to the supplied information. It is to be understood that the barcode can potentially include information that identifies activities engaged or completed together with physiological effects thereof. However, it is possible that actual physiological effects (e.g., calories burned) will not be included within the coded information. Here, the information access component 1104 can be employed to gain access to this information from some external source (e.g., Internet, cloud). Thus, a complete set of information can be logged within the activity log (e.g., 708 of FIG. 7) for access and/or analysis.

Figure 12:
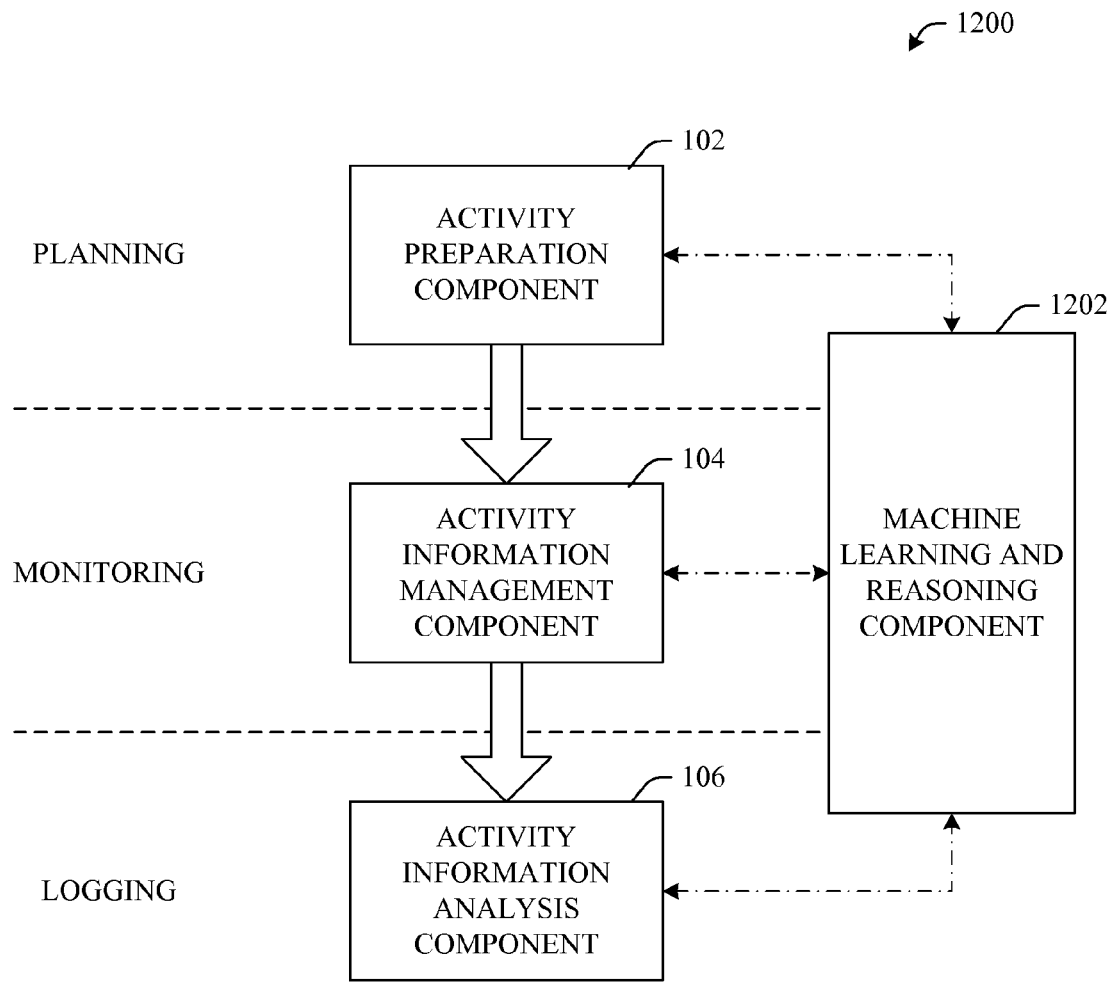
FIG. 12 illustrates an architecture including machine learning and reasoning-based component that can automate functionality in accordance with an aspect of the innovation.

FIG. 12 illustrates a system 1200 that employs an artificial intelligence (AI) or machine learning and reasoning component 1202 which facilitates automating one or more features in accordance with the subject innovation. The subject innovation (e.g., in connection with activity preparation/planning, indicia or protocol selection) can employ various AI-based schemes for carrying out various aspects thereof. For example, a process for determining what exercises to incorporate into a regimen or what type of indicia to employ or what protocol to use to communicate the information can be facilitated via an automatic classifier system and process.

A classifier is a function that maps an input attribute vector, x=(x1, x2, x3, x4, xn), to a confidence that the input belongs to a class, that is, f(x)=confidence(class). Such classification can employ a probabilistic and/or statistical-based analysis (e.g., factoring into the analysis utilities and costs) to prognose or infer an action that a user desires to be automatically performed.

A support vector machine (SVM) is an example of a classifier that can be employed. The SVM operates by finding a hypersurface in the space of possible inputs, which the hypersurface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and probabilistic classification models providing different patterns of independence can be employed. Classification as used herein also is inclusive of statistical regression that is utilized to develop models of priority.

As will be readily appreciated from the subject specification, the subject innovation can employ classifiers that are explicitly trained (e.g., via a generic training data) as well as implicitly trained (e.g., via observing user behavior, receiving extrinsic information). For example, SVM's are configured via a learning or training phase within a classifier constructor and feature selection module. Thus, the classifier(s) can be used to automatically learn and perform a number of functions, including but not limited to determining according to a predetermined criteria characteristics of a regimen in view of a particular goal, what effects contextual awareness will have on a regimen or performance thereof, what type of indicia or protocol to employ in a particular context, etc.

Figure 13:
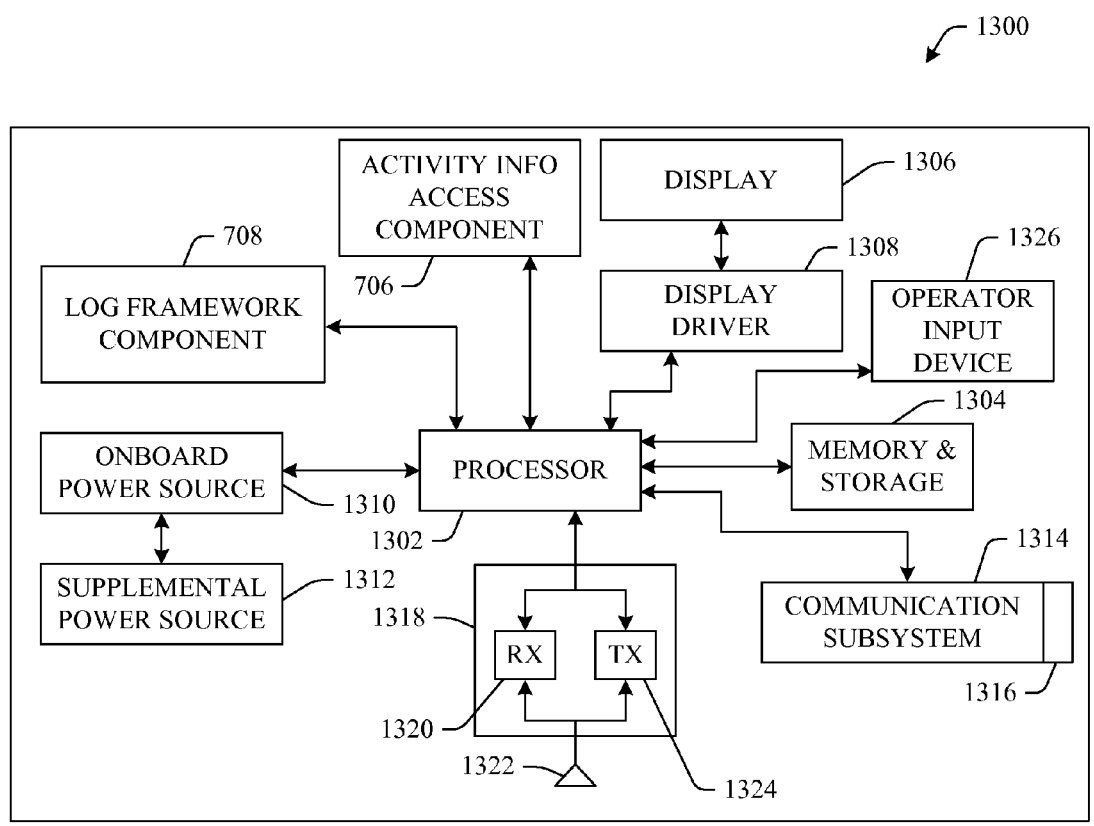
FIG. 13 illustrates a block diagram of an example mobile device that facilitates processing identifying indicia in accordance with an aspect of the innovation.

Referring now to FIG. 13, there is illustrated a schematic block diagram of a portable device 1300 according to one aspect of the subject innovation, in which a processor 1302 is responsible for controlling the general operation of the device 1300. It is to be understood that the portable device 1300 can be representative of most any portable device including, but not limited to, a cell phone, smartphone, personal digital assistant (PDA), a personal music player, image capture device (e.g., camera), personal game station, health monitoring device, event recorder component, etc.

The processor 1302 can be programmed to control and operate the various components within the device 1300 in order to carry out the various functions described herein. The processor 1302 can be any of a plurality of suitable processors. The manner in which the processor 1302 can be programmed to carry out the functions relating to the subject innovation will be readily apparent to those having ordinary skill in the art based on the description provided herein. As was described in greater detail supra, an MLR component can be used to effect an automatic action of processor 1302.

A memory and storage component 1304 connected to the processor 1302 serves to store program code executed by the processor 1302, and also serves as a storage means for storing information such as data, services, metadata, device states or the like. In aspects, this memory and storage component 1304 can be employed in conjunction with other memory mechanisms that house activity-related data, for example, log framework component 708. As well, in other aspects, the memory and storage component 1304 can be a stand-alone storage device or otherwise synchronized with a cloud or disparate network based storage means, thereby establishing a local on-board storage of activity-related data.

The memory 1304 can be a non-volatile memory suitably adapted to store at least a complete set of the information that is acquired. Thus, the memory 1304 can include a RAM or flash memory for high-speed access by the processor 1302 and/or a mass storage memory, e.g., a micro drive capable of storing gigabytes of data that comprises text, images, audio, and video content. According to one aspect, the memory 1304 has sufficient storage capacity to store multiple sets of information relating to disparate services, and the processor 1302 could include a program for alternating or cycling between various sets of information corresponding to disparate services.

A display 1306 can be coupled to the processor 1302 via a display driver system 1308. The display 1306 can be a color liquid crystal display (LCD), plasma display, touch screen display or the like. In one example, the display 1306 is a touch screen display. The display 1306 functions to present data, graphics, or other information content. Additionally, the display 1306 can display a variety of functions that control the execution of the device 1300. For example, in a touch screen example, the display 1306 can display touch selection buttons which can facilitate a user to interface more easily with the functionalities of the device 1300.

Power can be provided to the processor 1302 and other components forming the device 1300 by an onboard power system 1310 (e.g., a battery pack). In the event that the power system 1310 fails or becomes disconnected from the device 1300, a supplemental power source 1312 can be employed to provide power to the processor 1302 (and other components (e.g., sensors, image capture device)) and to charge the onboard power system 1310. The processor 1302 of the device 1300 can induce a sleep mode to reduce the current draw upon detection of an anticipated power failure.

The device 1300 includes a communication subsystem 1314 having a data communication port 1316, which is employed to interface the processor 1302 with a remote computer, server, service, or the like. The port 1316 can include at least one of Universal Serial Bus (USB) and IEEE 1394 serial communications capabilities. Other technologies can also be included, but are not limited to, for example, infrared communication utilizing an infrared data port, Bluetooth™, etc.

The device 1300 can also include a radio frequency (RF) transceiver section 1318 in operative communication with the processor 1302. The RF section 1318 includes an RF receiver 1320, which receives RF signals from a remote device via an antenna 1322 and can demodulate the signal to obtain digital information modulated therein. The RF section 1318 also includes an RF transmitter 1324 for transmitting information (e.g., data, service) to a remote device, for example, in response to manual user input via a user input 1326 (e.g., a keypad) or automatically in response to a detection of entering and/or anticipation of leaving a communication range or other predetermined and programmed criteria.

An activity information access component 706 is provided which, as described supra, can facilitate access and/or management of user-specific activity data. A log framework component 708 can be employed to define format and/or store activity information within the device 1300. It is to be appreciated that these components can enable functionality of like-named components (and sub-components) described supra.

Figure 14:
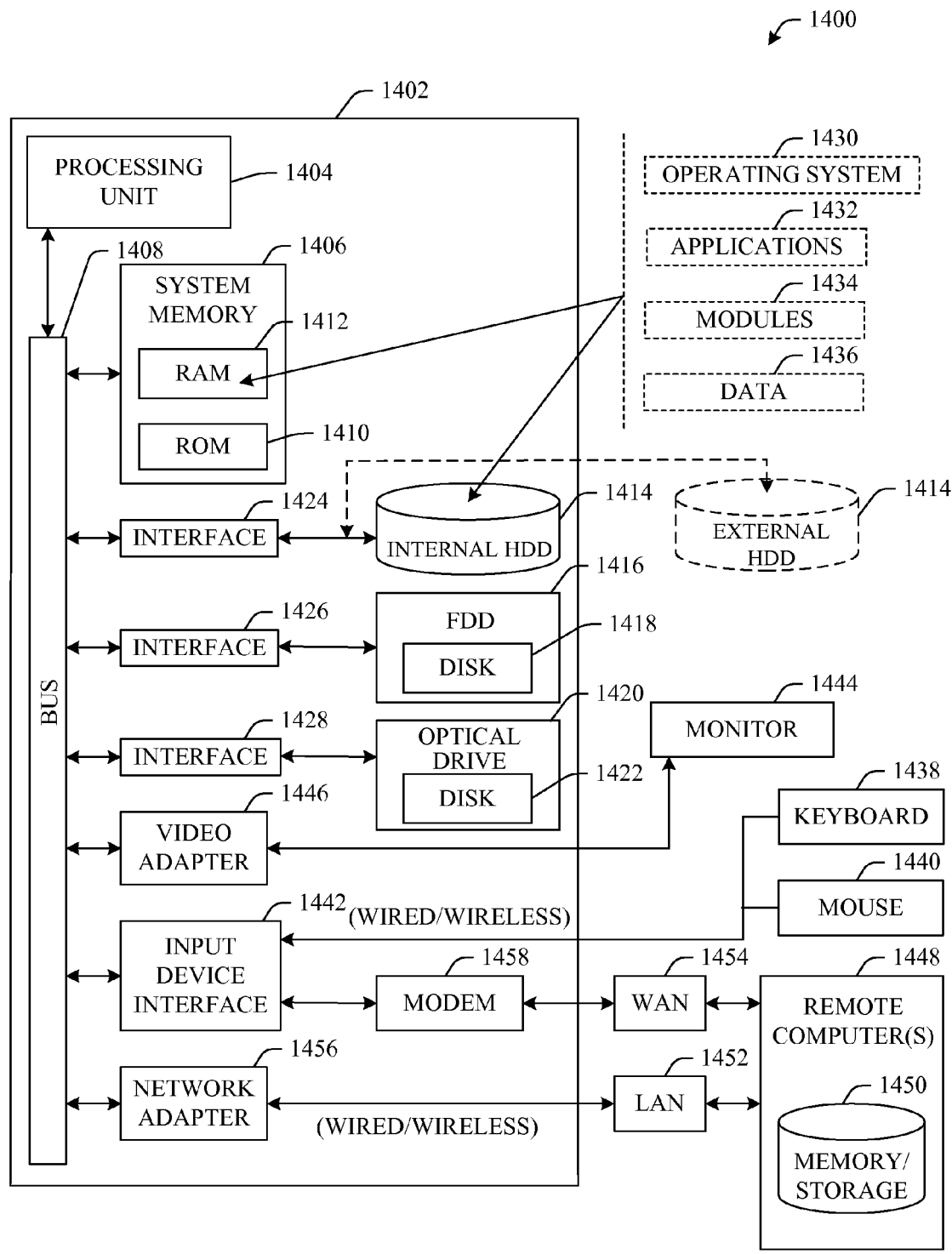
FIG. 14 illustrates a block diagram of a computer operable to execute the disclosed architecture.

Referring now to FIG. 14, there is illustrated a block diagram of a computer operable to execute the disclosed architecture. In order to provide additional context for various aspects of the subject innovation, FIG. 14 and the following discussion are intended to provide a brief, general description of a suitable computing environment 1400 in which the various aspects of the innovation can be implemented. While the innovation has been described above in the general context of computer-executable instructions that may run on one or more computers, those skilled in the art will recognize that the innovation also can be implemented in combination with other program modules and/or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, as well as personal computers, hand-held computing devices, microprocessor-based or programmable consumer electronics, and the like, each of which can be operatively coupled to one or more associated devices.

The illustrated aspects of the innovation may also be practiced in distributed computing environments where certain tasks are performed by remote processing devices that are linked through a communications network. In a distributed computing environment, program modules can be located in both local and remote memory storage devices.

A computer typically includes a variety of computer-readable media. Computer-readable media can be any available media that can be accessed by the computer and includes both volatile and nonvolatile media, removable and non-removable media. By way of example, and not limitation, computer-readable media can comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or any other medium which can be used to store the desired information and which can be accessed by the computer.

Communication media typically embodies computer-readable instructions, data structures, program modules or other data in a modulated data signal such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer-readable media.

With reference again to FIG. 14, the exemplary environment 1400 for implementing various aspects of the innovation includes a computer 1402, the computer 1402 including a processing unit 1404, a system memory 1406 and a system bus 1408. The system bus 1408 couples system components including, but not limited to, the system memory 1406 to the processing unit 1404. The processing unit 1404 can be any of various commercially available processors. Dual microprocessors and other multi-processor architectures may also be employed as the processing unit 1404.

The system bus 1408 can be any of several types of bus structure that may further interconnect to a memory bus (with or without a memory controller), a peripheral bus, and a local bus using any of a variety of commercially available bus architectures. The system memory 1406 includes read-only memory (ROM) 1410 and random access memory (RAM) 1412. A basic input/output system (BIOS) is stored in a non-volatile memory 1410 such as ROM, EPROM, EEPROM, which BIOS contains the basic routines that help to transfer information between elements within the computer 1402, such as during start-up. The RAM 1412 can also include a high-speed RAM such as static RAM for caching data.

The computer 1402 further includes an internal hard disk drive (HDD) 1414 (e.g., EIDE, SATA), which internal hard disk drive 1414 may also be configured for external use in a suitable chassis (not shown), a magnetic floppy disk drive (FDD) 1416, (e.g., to read from or write to a removable diskette 1418) and an optical disk drive 1420, (e.g., reading a CD-ROM disk 1422 or, to read from or write to other high capacity optical media such as the DVD). The hard disk drive 1414, magnetic disk drive 1416 and optical disk drive 1420 can be connected to the system bus 1408 by a hard disk drive interface 1424, a magnetic disk drive interface 1426 and an optical drive interface 1428, respectively. The interface 1424 for external drive implementations includes at least one or both of Universal Serial Bus (USB) and IEEE 1394 interface technologies. Other external drive connection technologies are within contemplation of the subject innovation.

The drives and their associated computer-readable media provide nonvolatile storage of data, data structures, computer-executable instructions, and so forth. For the computer 1402, the drives and media accommodate the storage of any data in a suitable digital format. Although the description of computer-readable media above refers to a HDD, a removable magnetic diskette, and a removable optical media such as a CD or DVD, it should be appreciated by those skilled in the art that other types of media which are readable by a computer, such as zip drives, magnetic cassettes, flash memory cards, cartridges, and the like, may also be used in the exemplary operating environment, and further, that any such media may contain computer-executable instructions for performing the methods of the innovation.

A number of program modules can be stored in the drives and RAM 1412, including an operating system 1430, one or more application programs 1432, other program modules 1434 and program data 1436. All or portions of the operating system, applications, modules, and/or data can also be cached in the RAM 1412. It is appreciated that the innovation can be implemented with various commercially available operating systems or combinations of operating systems.

A user can enter commands and information into the computer 1402 through one or more wired/wireless input devices, e.g., a keyboard 1438 and a pointing device, such as a mouse 1440. Other input devices (not shown) may include a microphone, an IR remote control, a joystick, a game pad, a stylus pen, touch screen, or the like. These and other input devices are often connected to the processing unit 1404 through an input device interface 1442 that is coupled to the system bus 1408, but can be connected by other interfaces, such as a parallel port, an IEEE 1394 serial port, a game port, a USB port, an IR interface, etc.

A monitor 1444 or other type of display device is also connected to the system bus 1408 via an interface, such as a video adapter 1446. In addition to the monitor 1444, a computer typically includes other peripheral output devices (not shown), such as speakers, printers, etc.

The computer 1402 may operate in a networked environment using logical connections via wired and/or wireless communications to one or more remote computers, such as a remote computer(s) 1448. The remote computer(s) 1448 can be a workstation, a server computer, a router, a personal computer, portable computer, microprocessor-based entertainment appliance, a peer device or other common network node, and typically includes many or all of the elements described relative to the computer 1402, although, for purposes of brevity, only a memory/storage device 1450 is illustrated. The logical connections depicted include wired/wireless connectivity to a local area network (LAN) 1452 and/or larger networks, e.g., a wide area network (WAN) 1454. Such LAN and WAN networking environments are commonplace in offices and companies, and facilitate enterprise-wide computer networks, such as intranets, all of which may connect to a global communications network, e.g., the Internet.

When used in a LAN networking environment, the computer 1402 is connected to the local network 1452 through a wired and/or wireless communication network interface or adapter 1456. The adapter 1456 may facilitate wired or wireless communication to the LAN 1452, which may also include a wireless access point disposed thereon for communicating with the wireless adapter 1456.

When used in a WAN networking environment, the computer 1402 can include a modem 1458, or is connected to a communications server on the WAN 1454, or has other means for establishing communications over the WAN 1454, such as by way of the Internet. The modem 1458, which can be internal or external and a wired or wireless device, is connected to the system bus 1408 via the serial port interface 1442. In a networked environment, program modules depicted relative to the computer 1402, or portions thereof, can be stored in the remote memory/storage device 1450. It will be appreciated that the network connections shown are exemplary and other means of establishing a communications link between the computers can be used.

The computer 1402 is operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, restroom), and telephone. This includes at least Wi-Fi and Bluetooth™ wireless technologies. Thus, the communication can be a predefined structure as with a conventional network or simply an ad hoc communication between at least two devices.

Wi-Fi, or Wireless Fidelity, allows connection to the Internet from a couch at home, a bed in a hotel room, or a conference room at work, without wires. Wi-Fi is a wireless technology similar to that used in a cell phone that enables such devices, e.g., computers, to send and receive data indoors and out; anywhere within the range of a base station. Wi-Fi networks use radio technologies called IEEE 802.11 (a, b, g, etc.) to provide secure, reliable, fast wireless connectivity. A Wi-Fi network can be used to connect computers to each other, to the Internet, and to wired networks (which use IEEE 802.3 or Ethernet). Wi-Fi networks operate in the unlicensed 2.4 and 5 GHz radio bands, at an 11 Mbps (802.11a) or 54 Mbps (802.11b) data rate, for example, or with products that contain both bands (dual band), so the networks can provide real-world performance similar to the basic 10BaseT wired Ethernet networks used in many offices.

Figure 15:
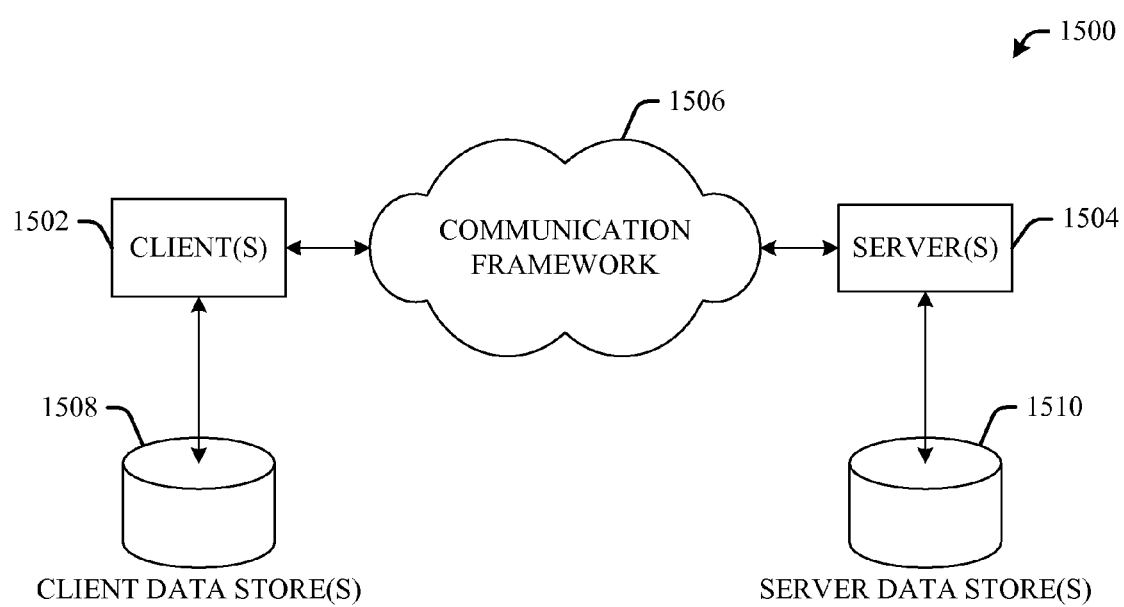
FIG. 15 illustrates a schematic block diagram of an exemplary computing environment in accordance with the subject innovation.

Referring now to FIG. 15, there is illustrated a schematic block diagram of an exemplary computing environment 1500 in accordance with the subject innovation. The system 1500 includes one or more client(s) 1502. The client(s) 1502 can be hardware and/or software (e.g., threads, processes, computing devices). The client(s) 1502 can house cookie(s) and/or associated contextual information by employing the innovation, for example.

The system 1500 also includes one or more server(s) 1504. The server(s) 1504 can also be hardware and/or software (e.g., threads, processes, computing devices). The servers 1504 can house threads to perform transformations by employing the innovation, for example. One possible communication between a client 1502 and a server 1504 can be in the form of a data packet adapted to be transmitted between two or more computer processes. The data packet may include a cookie and/or associated contextual information, for example. The system 1500 includes a communication framework 1506 (e.g., a global communication network such as the Internet) that can be employed to facilitate communications between the client(s) 1502 and the server(s) 1504.

Communications can be facilitated via a wired (including optical fiber) and/or wireless technology. The client(s) 1502 are operatively connected to one or more client data store(s) 1508 that can be employed to store information local to the client(s) 1502 (e.g., cookie(s) and/or associated contextual information). Similarly, the server(s) 1504 are operatively connected to one or more server data store(s) 1510 that can be employed to store information local to the servers 1504.

What has been described above includes examples of the innovation. It is, of course, not possible to describe every conceivable combination of components or methodologies for purposes of describing the subject innovation, but one of ordinary skill in the art may recognize that many further combinations and permutations of the innovation are possible. Accordingly, the innovation is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A system for facilitating activity management, comprising:
    an activity preparation component configured to incorporate a predefined regimen of activity into configuration indicia, the activity preparation component including
        a regimen generation component configured to facilitate planning of an exercise or activity regimen that addresses one or more particular goals, at least in part by consideration of physiological parameters associated with the one or more particular goals, and by consideration of availability of exercise devices,
        an indicia generation component configured to incorporate regimen information corresponding to the regimen into transferable indicia or a medium, and
        a communication component configured to communicate the regimen information from the transferable indicia or medium to an apparatus; and
    an activity information management component configured to interpret the configuration indicia and calibrate the apparatus as a function of the regimen information, the activity information management component including
        an indicia management component configured to select a type of the transferable indicia or medium, and to aggregate activity information corresponding to the regimen, the activity information including at least physiological effects of the regimen, and to subsequently generate indicia corresponding to the activity information, and
        a communication component configured to communicate the activity information, via the generated indicia, to a receiving device.

2. The system of claim 1, wherein the transferable indicia or medium includes one of a barcode, magnetic strip, radio frequency identification tag (RFID) or memory device.

3. The system of claim 1, wherein the regimen generating facilitates identification of a plurality of events that define the regimen.

4. The system of claim 1, wherein the activity information management component is further configured to dynamically monitor the activity information and adjust the apparatus to compensate if the activity information indicates a deviation from the regimen.

5. The system of claim 1, wherein the indicia management component comprises an indicia type selection component configured to select a manner in which to convey the activity information.

6. The system of claim 1, wherein the communication component of the activity preparation component is configured to transfer the configuration indicia to the activity information management component.

7. The system of claim 1, wherein the indicia management component is configured to encode the activity information into progress indicia, and the communication component of the activity information management component is configured to convey the progress indicia to a logging entity.

8. The system of claim 7, further comprising:
an information monitor component configured to dynamically monitor the activity information via the apparatus; and
an information aggregation component configured to compile the activity information, wherein the activity information represents a subset of a plurality of events.

9. The system of claim 7, wherein the indicia generation component is configured to establish the progress indicia.

10. The system of claim 9, further comprising an indicia analysis component configured to evaluate the progress indicia and determine a method of rendering the progress indicia.

11. The system of claim 9, further comprising a rendering component configured to deliver the progress indicia to the logging entity.

12. The system of claim 11, further comprising a protocol selection component configured to choose a protocol type by which to deliver the progress indicia, wherein the protocol type includes at least one of instant message, email, short message service (SMS), Bluetooth transfer, peer-to-peer or infrared transfer.

13. The system of claim 7, further comprising an activity information access component configured to employ an indicia processing component that obtains the activity information by way of the progress indicia.

14. The system of claim 13, wherein the indicia processing component includes at least one of a scanner, radio frequency information tag reader, magnetic card reader, or browser.

15. The system of claim 13, further comprising a log framework component configured to format, categorize and maintain the activity information.

16. The system of claim 1, further comprising a machine learning and reasoning component configured to employ at least one of a probabilistic and a statistical-based analysis that infers an action that a user desires to be automatically performed.

17. A computer-readable non-transitory storage medium storing instructions that, if executed by a computing device, perform a method comprising:
preparing regimen information corresponding to a planned regimen of activity, the planned regimen taking into consideration at least physiological parameters associated with one or more particular goals, and availability of exercise devices;
selecting transferable indicia or a medium to communicate the regimen information;
incorporating the regimen information in the selected transferable indicia or medium;
communicating the regimen information via the transferable indicia or medium to an apparatus;
interpreting the regimen information of the transferable indicia or medium to calibrate the apparatus;
aggregating activity information corresponding to the regimen and generated by the apparatus, the activity information including at least physiological effects of the regimen;
generating indicia corresponding to the activity information; and
communicating the activity information, via the generated indicia, to a receiving device.

18. The computer-readable medium of claim 17, the method further comprising monitoring the activity information via the apparatus.

19. The computer-readable medium of claim 17, the method further comprising conveying progress indicia associated with the regimen to a logging entity.

20. The computer-readable medium of claim 17, the method further comprising:
dynamically monitoring the activity information; and
adjusting the apparatus to compensate if the activity information indicates a deviation from the regimen.

* * * * *